United States Patent [19]

Rexroth

[11] Patent Number: 4,473,075
[45] Date of Patent: Sep. 25, 1984

[54] ELECTROSURGICAL GENERATOR WITH IMPROVED RAPID START CAPABILITY

[75] Inventor: Frederick W. Rexroth, Dunedin, Fla.

[73] Assignee: Medical Research Associates, Ltd., Clearwater, Fla.

[21] Appl. No.: 447,808

[22] Filed: Dec. 8, 1982

[51] Int. Cl.³ .............................................. A61B 12/39
[52] U.S. Cl. ............................ 128/303.14; 128/303.17
[58] Field of Search ..................... 128/303.13, 303.14, 128/303.16, 303.17

[56] References Cited

U.S. PATENT DOCUMENTS

| | | | |
|---|---|---|---|
| 4,038,984 | 8/1977 | Sittner | 128/303.14 |
| 4,188,927 | 2/1980 | Harris | 128/303.17 |
| 4,321,926 | 3/1982 | Roge | 128/303.18 |
| 4,378,801 | 4/1983 | Oosten | 128/303.14 |

Primary Examiner—Lee S. Cohen
Assistant Examiner—Steven Falk
Attorney, Agent, or Firm—Epstein & Edell

[57] ABSTRACT

An electrosurgical generator, having particular utility in arthroscopic surgical procedures, is provided with a rapid start capability in its pure cut mode by inhibiting secondary modulation for an initial starting interval during which an uninterrupted high frequency cutting signal is applied to the output terminals. Upon expiration of the starting interval, the secondary modulation takes effect to modulate the cutting signal with a low frequency repetitive signal having a predetermined duty cycle. In addition, the generator output isolation transformer is arranged to provide an output impedance of at least 1,000 Ohms to match the impedance of human joints on which arthroscopic surgery is performed.

20 Claims, 15 Drawing Figures

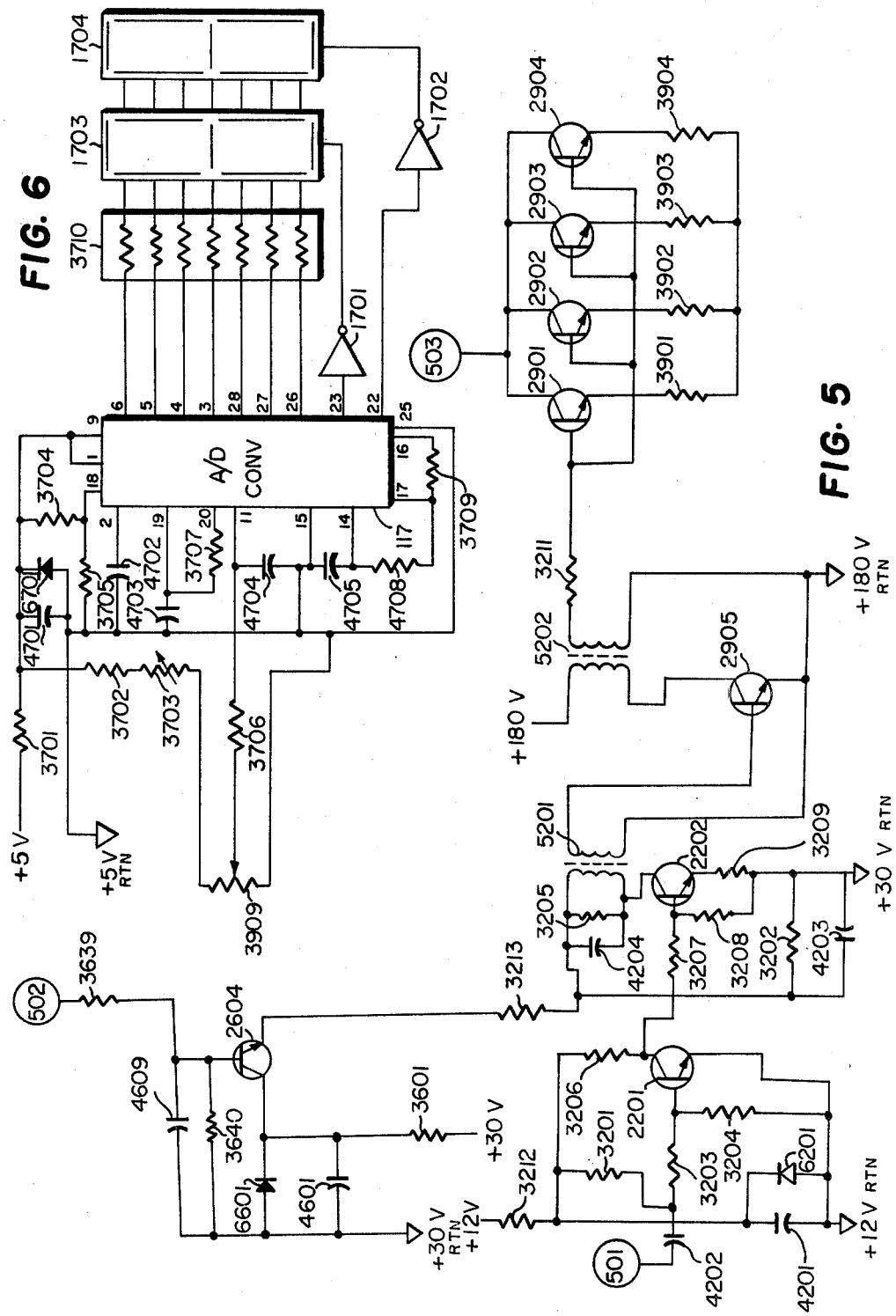

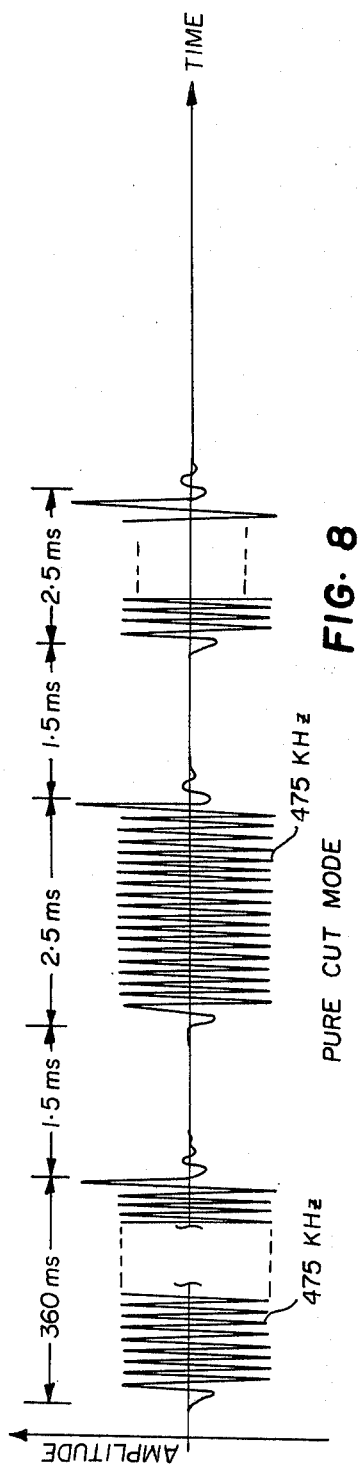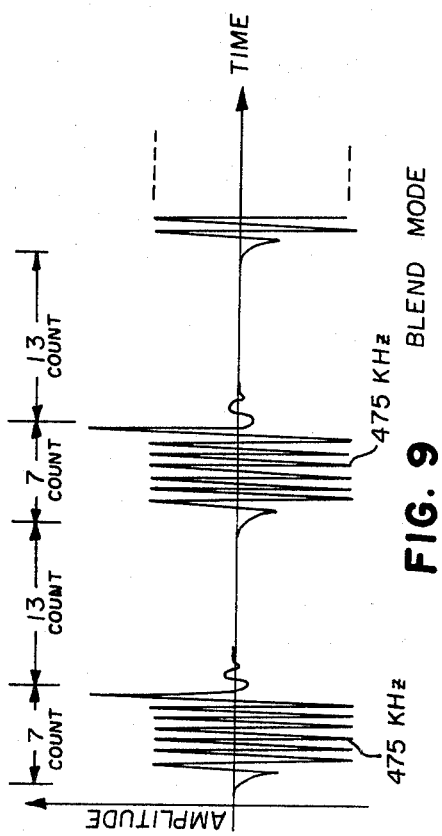

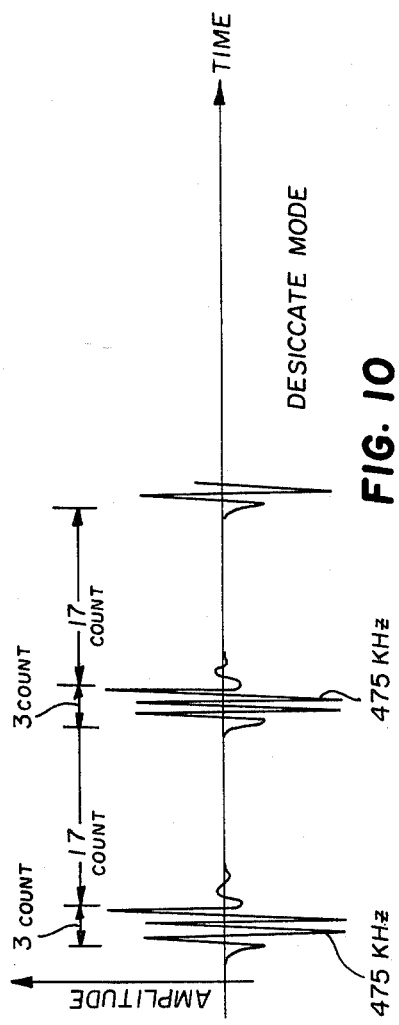
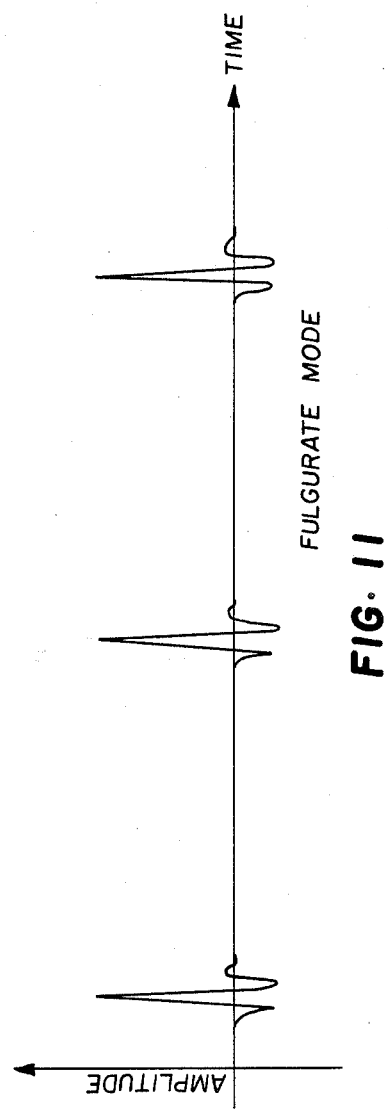

SECONDARY MODLATION

ELECTROSURGICAL GENERATOR WITH IMPROVED RAPID START CAPABILITY

BACKGROUND OF THE INVENTION

1. Technical Field

The present invention relates to electrosurgical generators and, more particularly, to electrosurgical generators having specific utility in arthroscopic surgical procedures.

2. The Prior Art

The prior art contains a variety of electrosurgical generators which utilize high frequency electrical signals to effect surgical cutting and/or coagulation. These signals are generally referred to as cutting signals, coagulation signals, or blend signals, the latter being formed by combining both the cutting and coagulation signals. The coagulation signals, in turn, may be subdivided into fulgurate and desiccate signals, depending upon the intended operating mode of the machine. Such signals are applied to a patient, conducted through the patient's body, and returned to the generator via a ground path.

The cutting signal is a high frequency signal which serves to cut through tissue when applied to the patient. An electrosurgical electrode is used to apply the electrical energy to defined and concentrated points of a patient's body. Cutting is accomplished by the concentrated application of high frequency electrical energy which effectively destroys the body cells directly beneath the electrosurgical electrodes. Coagulation signals are intended to produce coagulation by shrinking vessel walls. Typically, such coagulation signals are pulses of energy having a damped sinusoidal wave form. Coagulation signals may be viewed as causing cell dehydration to produce coagulation rather than destroying cells in the fashion of cutting signals. The blended signals are formed by combining the cutting and coagulation signals and are useful for accomplishing cutting and coagulation simultaneously. Alternating periods of each signal may be employed to form the blended signal.

There are many types of electrosurgical generators available in the prior art which are intended to function for general purpose surgery. Such generators are configured to efficiently cut into tissue impedances which range between three hundred to five hundred Ohms, and have output power levels which are typically in excess of three hundred watts. Such generators, however, are not efficient for performing surgery on the joints of the human body. One reason for this is the impedance presented by bony substances, cartilage, meniscus, etc., which impedance is considerably higher than that for which most general purpose electrosurgical generators are designed. When the impedance of the generator is not properly matched to the impedance of the human joint at the surgical site, the generator does not efficiently transfer energy to the surgical site and, therefore, relatively high power settings must be achieved to accomplish the desired surgical effect. These high energy settings can result in undesirable tissue damage, such as necrosis, in the vicinity of the operating area.

Another consideration affecting the inapplicability of most prior art electrosurgical generators for arthroscopic surgery relates to the slow start cutting characteristics of such generators. Specifically, arthroscopic knee surgery is performed in an irrigating media of water and requires that the electrosurgical generator be capable of cutting and coagulating under these conditions. When prior art electrosurgical generators are employed in wet fields or under water, they exhibit slow start cutting characteristics which surgeons generally refer to as a "delay" or "drag in cut". This effect can be overcome by the use of high power settings; however, after the cut is initiated, the energy delivered to the surgical site is much higher than required to sustain the desired cutting effect. One electrosurgical generator on the market provides a rapid start option in order to eliminate this cutting delay. However, the rapid start feature provided in such generator degrades the normal operating capabilities of the system.

OBJECTS AND SUMMARY OF THE INVENTION

It is a primary object of the present invention to provide an improved electrosurgical generator which is specifically designed to perform joint surgery and, more specifically, arthroscopic surgical procedures.

It is another object of the present invention to provide an electrosurgical generator capable of rapidly starting in wet fields or under water without the use of excessively high level signals that cause tissue damage.

A further object of the present invention is to provide an improved electrosurgical generator which is capable of rapidly starting when used in a wet field or under water and which, in the steady state cutting mode, provides a safe but efficient cutting signal level.

It is still another object of the present invention to provide an electrosurgical generator which efficiently transfers energy to a surgical site made up of bony substances, cartilage, meniscus, and other high electrical impedance substances.

In accordance with the present invention, the onset of a pure cut operating mode in an electrosurgical generator is characterized by the continuous or unmodulated application of the high frequency cutting signal to the surgical site for a predetermined initial time interval which, in the preferred embodiment, is on the order of 360 milliseconds. After the initial time interval terminates, low frequency modulation is applied to the high frequency cutting signal to alternately inhibit and pass the cutting signal to the surgical site at a predetermined duty cycle. The amplitude of the high frequency signal during the initial time interval is the same as the amplitude in the steady state condition, the only difference being the absence of modulation which results in the continuous application of the high frequency signal to the surgical site during start up. Continuous application of the cutting signal for the initial start up interval is effected by employing a one-shot multivibrator which is triggered by the onset of the pure cut mode to generate an output signal for the start up interval. This signal is utilized to inhibit low frequency secondary modulation of the high frequency cutting signal during the start up interval. The low frequency modulation is otherwise employed to modulate the cutting signal during the steady state pure cut mode and during all other operating modes.

In accordance with another feature of the present invention, an electrosurgical generator is provided with an isolation output transformer having an output impedance tuned to greater than 1,000 Ohms in order to provide an impedance match for the avascular, high impedance tissue of a human joint, and the turns ratio of the isolation transformer is selected to optimize the power transfer efficiency from the generator to the surgical site.

BRIEF DESCRIPTION OF THE DRAWINGS

The above and still further objects, features and advantages of the present invention will become apparent upon consideration of the following detailed description of specific embodiments thereof, especially when taken in conjunction with the accompanying drawings, wherein:

FIG. 5 is a schematic circuit diagram of the voltage controlled main amplifier 121 of FIG. 1;

FIG. 6 is a schematic circuit diagram of a digital display of the output level of the output control amplifiers of FIG. 3;

FIG. 8 is a plot of amplitude versus time of the output wave form generated in the pure cut mode of the present invention;

FIG. 9 is a plot of amplitude versus time of the wave form generated in the blend mode of the present invention;

FIG. 10 is a plot of amplitude versus time of the wave form generated in the desiccate mode of the present invention;

FIG. 11 is a plot of amplitude versus time of the fulgurate mode wave form generated in accordance with the present invention;

DESCRIPTION OF THE PREFERRED EMBODIMENTS

Figure 1:
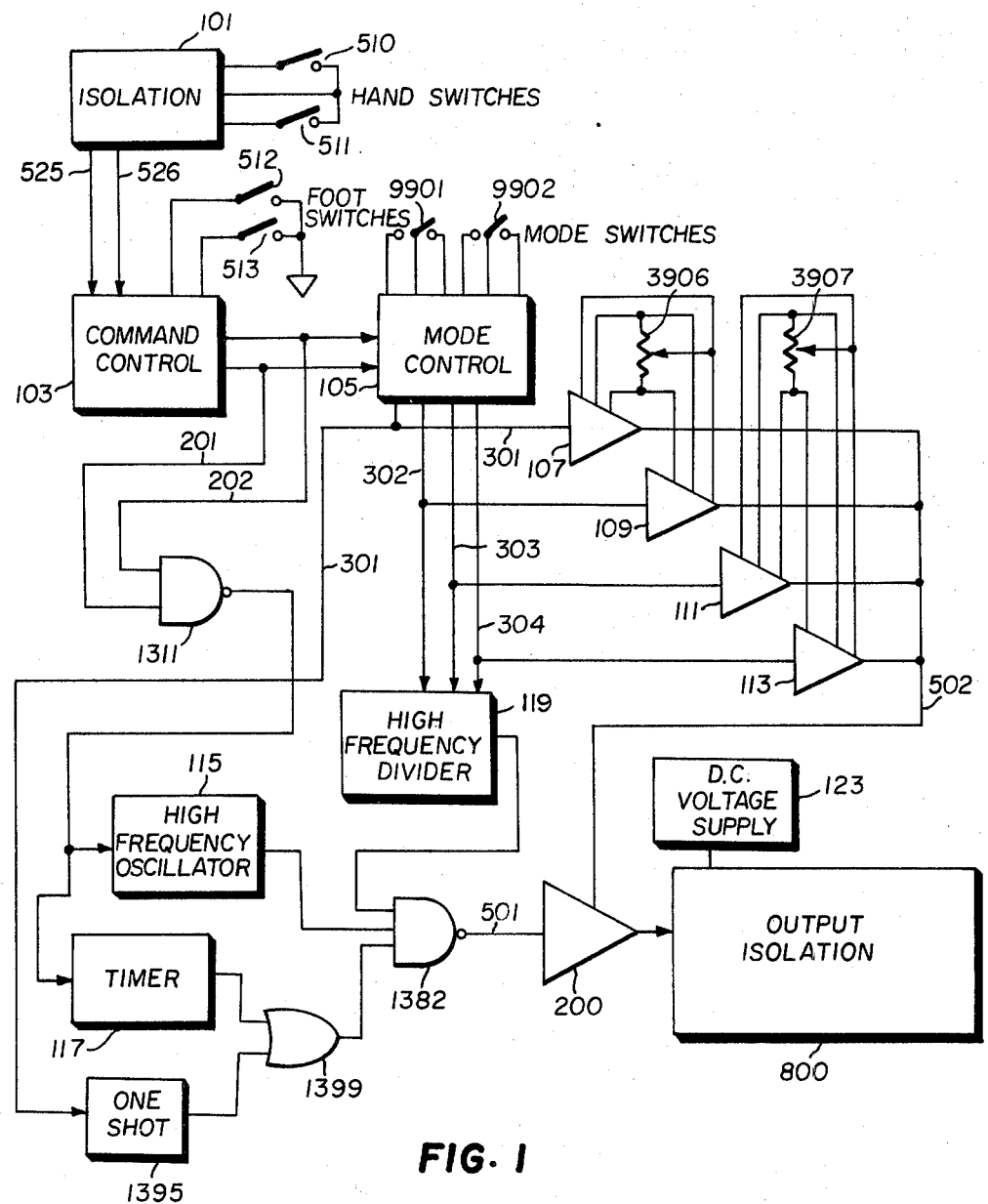
FIG. 1 is a partial functional block diagram and partial circuit schematic diagram showing one example of an electrosurgical generator according to the present invention.

The preferred embodiment of the present invention is illustrated in detail in FIGS. 1 through 7 of the accompanying drawings. Specific reference is now made to the functional block diagram of FIG. 1 wherein an electrosurgical generator is illustrated. The generator is capable of operating in four alternatively selectable modes in which four respective output signals are generated, namely, a pure cut signal, a blend signal, a fulgurate signal, and a desiccate signal. These four modes of operation may be subdivided into two command groups. A first group, which may be referred to as the cut command group, includes the pure cut and blend modes. The second group, which may be referred to as the coagulate command group, includes the fulgurate and desiccate modes. A treating physician may continuously select either the cut command or the coagulate command by using hand switches 510 and 511 or foot switches 512 and 513. The hand switches, which are most likely to come into electrical contact with the patient or physician during normal use, are isolated from the bulk of the electric circuit by isolation unit 101. If both the cut and coagulate commands are selected simultaneously by the physician, the command control 103 acts to terminate all functions until the command ambiguity is resolved. Absent such ambiguity, the command control unit 103 activates command line 201 if the cut command is chosen, or command line 202 if the coagulate command is chosen.

The activated command line energizes a corresponding circuit in the mode control unit 105, which circuit is controlled by either of the two mode switches 9901 and 9902. Switch 9901 is associated with the cut command line 201 and permits the operator to choose between two cut modes, namely pure and blend. Switch 9902 is associated with the coagulate command line 202 and permits the operator to choose between two coagulate modes, namely desiccate and fulgurate. Only one of the two command lines 201 and 202 can be active at any time. Therefore, only one of the four mode output lines 301, 302, 303 and 304 from the mode control unit 105 are active at any time. Mode line 301 is active for the pure cut mode, mode line 302 is active for the blend mode, mode line 303 is active for the desiccate mode and mode line 304 is active for the fulgurate mode.

The active mode line enables a respective output control amplifier 107, 109, 111 and 113. These amplifiers provide a voltage which controls the output gain of the main output amplifier 200. Amplifiers 107 and 109 control the cut mode output levels and are controlled by potentiometer 3906. Amplifiers 111 and 113 control the output level for the two coagulate functions and are controlled by potentiometer 3907.

Activation of either of the two command lines 201 or 202 causes NAND gate 1311 to activate the fixed high frequency oscillator 115 and the secondary modulation timer/oscillator 117. The output of the fixed high frequency oscillator 115, which is preferably at a frequency of 475 KHz, is gated through NAND gate 1382 to main amplifier 200. Variable high frequency divider 119 provides the primary modulation of the high frequency signal by counting output pulses of the fixed high frequency oscillator 115 and periodically interrupting the output of NAND gate 1382 in accordance with prescribed counting logic. The operation of the variable frequency divider and its associated logic is described in detail below in relation to FIG. 4.

The output of NAND gate 1382 is also periodically interrupted by the signal from oscillator/timer 117 to provide a secondary modulation of the high frequency signal at gate 1382. The timer/oscillator 117 operates at a fixed frequency which is very much lower than the fixed frequency of the high frequency oscillator 115. Typically, the frequency of the signal provided by oscillator/timer 117 is 250 Hz.

In accordance with the present invention, in the pure cut mode, the onset of the pure cut command signal on line 301 triggers a one-shot multivibrator 1395 which responds with a pulse of predetermined duration that is passed through OR gate 1399 to another input of NAND gate 1382. For the duration of the predetermined interval of the one-shot pulse, the effect of the low frequency modulation signal from timer 117 is effectively negated at NAND gate 1382 so that the high frequency signal from oscillator 115 passes through that gate without secondary modulation. Upon termination of the output pulses from one-shot multivibrator 1395, the cyclic waveform from oscillator/timer 117 controls passage of the high frequency signal from oscillator 115 through gate 1382. Therefore, for the pure cut mode, there is a delay, controlled by one-shot multivibrator 1395, before secondary modulation is applied to the high frequency signal. The secondary modulation is only applied during the steady state portion of the pure cut mode and not during the initial start up portion of that mode. This technique provides the extra energy level required to initiate and incise quickly without having to sustain that high energy level throughout the duration of the incision. It can be readily seen, therefore, that the present invention permits surgical incisions to be performed at much lower power settings, thereby reducing the risk of undesired tissue destruction. One-shot multivibrator 1395 is only actuated during the start up portion of the pure cut mode and does not affect operation in any of the other three modes.

The output of NAND gate 1382 is fed to the input of main amplifier 200. As previously noted, the output level of the main amplifier 200 is set by the output signals from the activated output controlled amplifier 107, 109, 111 or 113. The main amplifier output signal draws current from the d.c. voltage source 123 through the output isolation unit 800. The treating physician may choose between bipolar and monopolar output configuration by making appropriate connections between the patient electrodes and the output isolation unit 800.

Figure 7:
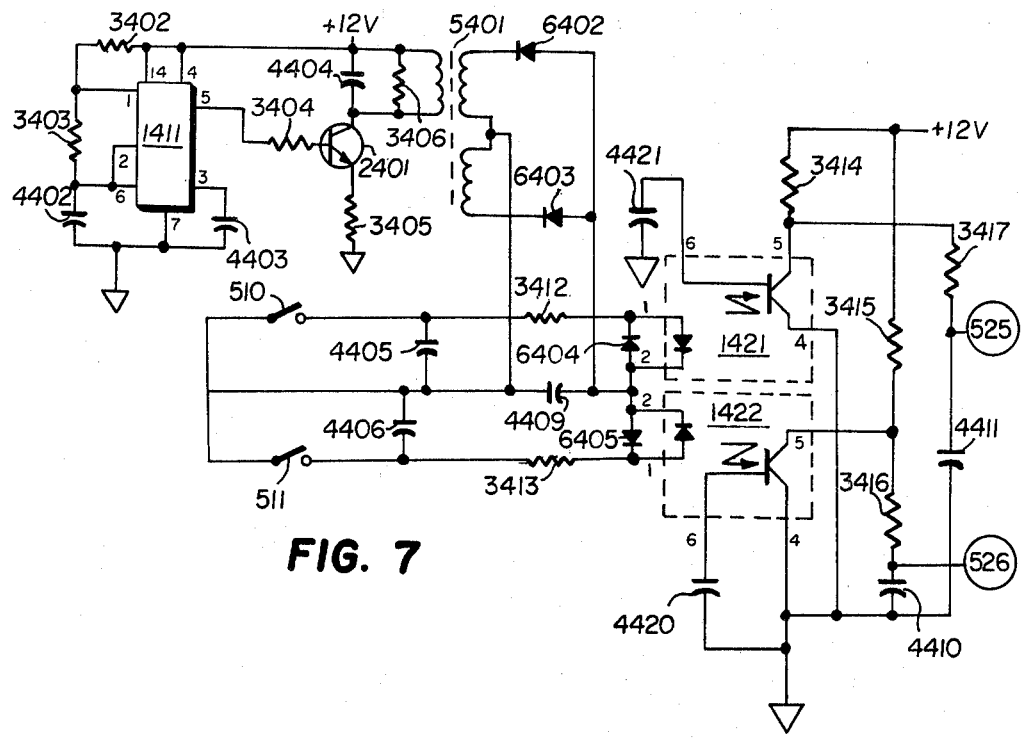
FIG. 7 is a schematic circuit diagram of the isolation unit 101 of FIG. 1.

The circuit illustrated in FIG. 7 represents the isolation circuit 101 of FIG. 1 and serves to isolate and reduce rf leakage between hand-held command switches 510, 511 and the command control unit 103. This isolation circuit consists of an audio frequency oscillator, preferably operating at 23 KHz, which periodically triggers NPN transistor 2401. The oscillator is formed by timer 1411, which is typically a standard 556 integrated circuit timer having 12 volts supplied to pins 4 and 14. Resistor 3402 is connected between pins 1 and 14, whereas resistor 3403 is connected between pins 1 and 6, and pins 2 and 6 are connected together. Capacitors 4402 and 4403 connect pins 6 and 3, respectively, to the 12 volt return path or ground. Pin 7 is directly connected to the 12 volt return path.

The output of timer 1411 passes from output pin 5 through resistor 3404 to the base of transistor 2401. Resistor 3405 couples the emitter of transistor 2401 to ground. The collector of transistor 2401 is coupled to the 12 volt supply through the parallel combination of capacitor 4404, resistor 3406 and the primary winding of transformer 5401. As the oscillator repetitively triggers transistor 2401, current is alternately blocked and passed through the primary winding of transformer 5401. The cathodes of diodes 6402 and 6403 are coupled to the side taps of the secondary winding of transformer 5401. Capacitor 4409 couples the center tap of the secondary winding of transformer 5401 to the anodes of diodes 6402 and 6403. The center tap is further coupled directly to the common line which interconnects hand switches 510 and 511. Capacitor 4405 couples the center tap of the secondary winding of transformer 5401 to the junction between switch 510 and resistor 3412. Switch 510 is connected through resistor 3412 to pin 1 of an opto-isolator 1421. Diode 6404 is connected cathode-to-anode between pins 1 and 2 of opto-isolator 1421; pin 2 is also connected to the anodes of diodes 6402 and 6403. Similarly, capacitor 4406 couples the center tap of the secondary winding of transformer 5401 to the junction between switch 511 and resistor 3413. Switch 511 is connected through resistor 3413 to pin 1 of opto-isolator 1422; pin 1 is also connected through diode 6405 to pin 2 of opto-isolator 1421 and to the anodes of diodes 6402 and 6403.

Opto-isolator 1421 is connected to the circuit ground at pin 4. Pin 5 is the output pin for switch 510 and is connected through resistor 3414 to the 12 volt supply and also through resistor 3417 to signal line 525 and capacitor 4411, the latter being connected to ground. Pin 6 is coupled through capacitor 4421 to ground. Likewise, opto-isolator 1422 is grounded to circuit ground at pin 4. Pin 5 of opto-isolator 1422 is the output pin for switch 511 and is connected through resistor 3415 to the 12 volt supply as well as through resistor 3416 to line 526 and capacitor 4410, the latter being connected to ground. Pin 6 is coupled through capacitor 4420 to ground.

The secondary voltage of the transformer 5401 is full wave rectified and filtered to provide a d.c. voltage by diodes 6402 and 6403 and capacitor 4409. Resistors 3412 and 3413 limit the small amount of d.c. current supplied to the hand switches and the input diodes of opto-isolators 1421 and 1422. For example, when the cut command group is activated by closing switch 510, current flows through resistor 3412 and pins 1 and 2 of opto-isolator 1421, thereby causing the signal at pin 5 of opto-isolator 1421 to go low.

Figure 2:
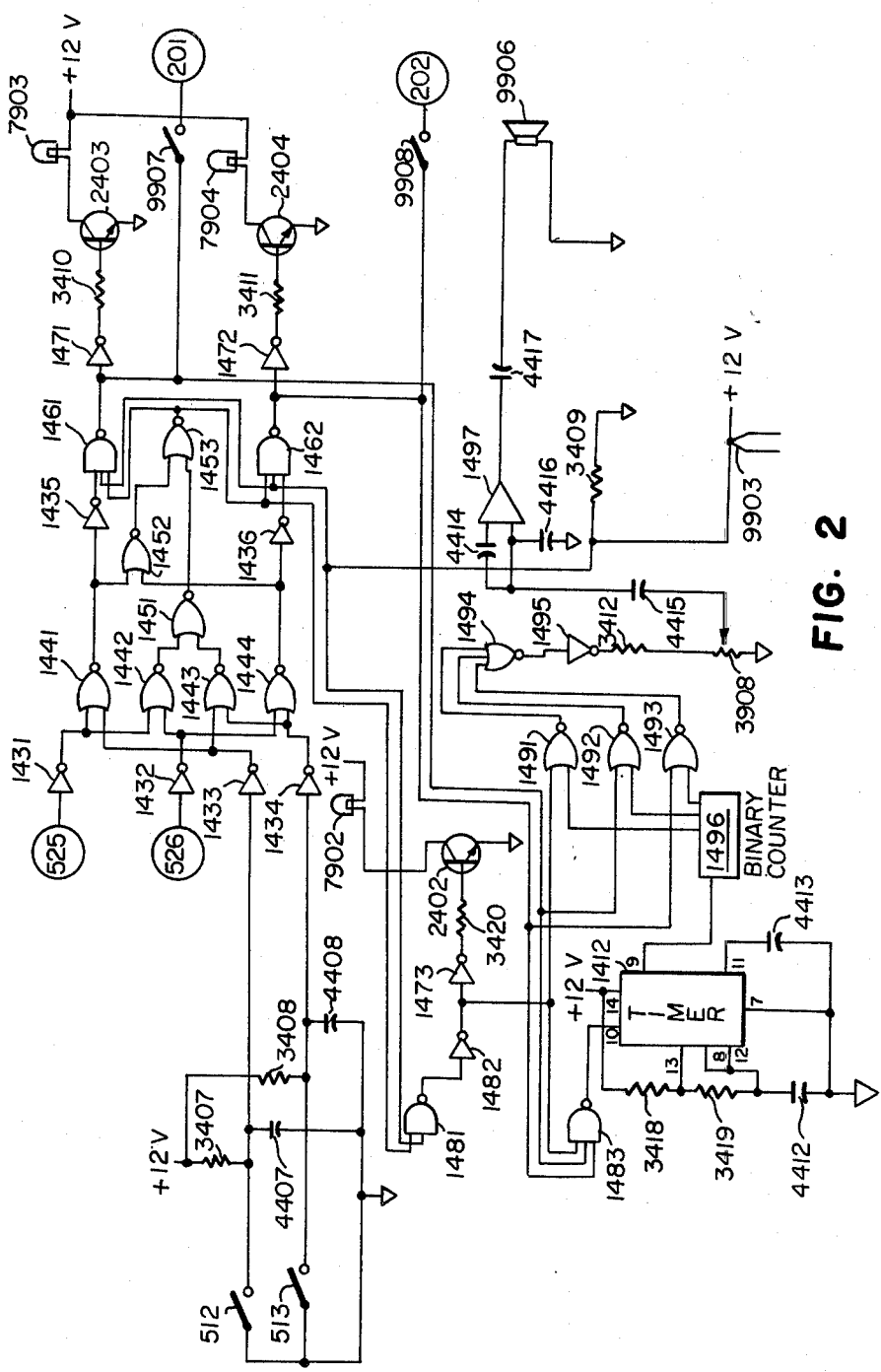
FIG. 2 is a schematic circuit diagram illustrating the command control unit 103 of FIG. 1.

Referring specifically to FIG. 2 of the accompanying drawings, the input signals for inverters 1431 and 1432 are connected to the circuits for the hand switches 510 and 511, respectively, via the isolation unit 101 of FIG. 7 and lines 525 and 526, respectively. The input signal for inverter 1433 is coupled through the parallel combination of switch 512 and capacitor 4407 to ground, and through resistor 3407 to a 12 volt supply. Likewise, the input signal for inverter 1434 is coupled through the parallel combination of switch 513 and capacitor 4408 to ground, and through resistor 3408 to the 12 volt supply. Therefore, the input signals for inverters 1433 and 1434 remain high unless a switch is closed, at which time the respective inverter input signal goes low and its output goes high.

The output signals from inverters 1431 and 1433 are coupled directly to the input terminals of NOR gate 1441. Therefore, when either or both of switches 510 and 512 are opened, the output of NOR gate 1441 goes low. The output signals from inverters 1432 and 1434 are coupled directly to the input terminals of NOR gate 1444. Theefore, when either or both of switches 511 and 513 are open, the output of NOR gate 1444 goes low.

The output signals from inverters 1431 and 1432 are also coupled to the input terminals of NOR gate 1442. When either or both of switches 510 and 511 are closed, the output of NOR gate 1442 goes low. The output of inverters 1433 and 1434 are coupled to the inputs of NOR gate 1443. When either or both of switches 510 and 511 are opened, the output of NOR gate 1443 goes low. The outputs of NOR gates 1442 and 1443 are coupled to the inputs of NOR gate 1451, and the outputs from NOR gates 1441 and 1444 are coupled to the inputs of NOR gate 1452. The output signals from NOR gates 1451 and 1452 are coupled to the input terminals of NOR gate 1453. The cut command may be indicated by closing either of switches 510 or 512, and the coagulate command may be indicated by closing either of switches 511 or 513. When any two switches are closed, indicating conflicting operating modes at the same time, the output of NOR gate 1453 goes low.

The output from NOR gate 1441 is coupled through inverter 1435 to one input of NAND gate 1461. The output of NOR gate 1453 is connected to another input of NAND gate 1461, and the output of a thermostat 9903 is coupled to a third input of NAND gate 1461. Thus, when the output of inverter 1435 is high, indicating a cut command condition, and the output of NOR gate 1453 is high, indicating no conflicting command, and the output of thermostat 9903 is high, indicating no heat overload, then the output of NAND gate 1461 goes low to activate the command line 201 via switch 9907. If the output of NOR gate 1453 goes low, or the output of thermostat 9903 goes low, the output of NAND gate 1461 goes high, thereby de-activating the command line 201.

The output signal from NAND gate 1461 is also coupled through inverter 1471 and resistor 3410 in series to the base of NPN transistor 2403. The emitter of transistor 2403 is grounded and its collector is coupled through lamp 7903 to a 12 volt supply. When NAND gate 1461 activates command line 201, the base of transistor 2403 goes high, thereby lighting lamp 7903 to indicate that cut command group operation is taking place.

Similarly, the output of NOR gate 1444 is coupled through inverter 1436 to one input of NAND gate 1462. The output signal from NOR gate 1453 is connected to another input of NAND gate 1462, and the output of thermostat 9903 is coupled to a third input of NAND gate 1462. When the output of inverter 1436 is high, thereby indicating a coagulate command condition, and the output of NOR gate 1453 is high, thereby indicating no conflicting command, and the output of thermostat 9903 is high, thereby indicating no heat overload, then the output of NAND gate 1462 is low, activating the command line 202 through switch 9908. If the output of NOR gate 1453 goes low, or the output of thermostat 9903 goes low, the output signal from NAND gate 1462 goes high, thereby de-activating command line 202.

The output signal from NAND gate 1462 is also coupled through inverter 1472 and resistor 3411 in series with the base of NPN transistor 2404. The emitter of transistor 2404 is grounded and the collector of transistor 2404 is coupled through lamp 7904 to a 12 volt supply. When NAND gate 1462 activates command line 202, the base of transistor 2404 goes high, thereby lighting lamp 7904 to indicate the existence of a coagulate command group operation.

The output signals from NOR gate 1453 and thermostat 9903 are also coupled to the input terminals of NAND gate 1481. The output signal from NAND gate 1481 is coupled through the series combination of inverters 1482, 1473 and resistor 3420 to the base of NPN transistor 2402. The emitter of transistor 2402 is grounded and its collector is connected through lamp 7902 to a 12 volt supply. If the output signal from either thermostat 9903 or NOR gate 1453 goes low, then the base of transistor 2402 goes high and current flows through lamp 7902 to indicate that the generator has automatically ceased operation.

The output signals from NAND gates 1461 and 1462 and from inverter 1482 are coupled to the input terminals of NAND gate 1483. The output of NAND gate 1483 is connected to pin 10 of integrated circuit 1412 which is a type 556 timer. If either command line 201 or 202 is activated, or if the generator is automatically shut down, the output from NAND gate 1483 goes high, thereby activating an oscillator formed by timer 1412 and the associated passive circuit components. Pin 14 of timer 1412 is connected to a 12 volt supply and to resistor 3418. The other side of resistor 3418 is connected to pin 13 of timer 1412. Pin 13 is also connected through resistor 3419 to pins 8 and 12. Pin 7 of timer 1412 is grounded; pin 11 is capacitively coupled to ground via capacitor 4413; and pins 8 and 12 are capacitively coupled to ground via capacitor 4412. The oscillator output signal from pin 9 of timer 1412 is connected to the count input terminal of binary counter 1496.

The binary counter 1496 divides the output frequency from the oscillator by three different fixed factors. Each of the three counter output signals are coupled to an input of two-input NOR gates 1491, 1492 and 1493, respectively. The output signal from inverter 1482 is coupled to the second input of NOR gate 1491, so that when NOR gate 1453 or thermostat 9903 cause a shut down, the output signal from NOR gate 1491 is the logic inverse of the associated input from counter 1496. Likewise, command line 201 is coupled to the second input terminal of NOR gate 1492, so that when command line 201 is activated, the output signal from NOR gate 1492 becomes the logic inverse of the associated input signal from counter 1496. Further, command line 202 is coupled to the second input terminal of NOR gate 1493, so that when command line 202 is activated, the output from NOR gate 1493 becomes the logic inverse of the associated input from counter 1496.

The output signals from NOR gates 1491, 1492 and 1493 are coupled to the inputs of NOR gate 1494. Thus, the output of NOR gate 1494 represents the status of the generator: either cut command, coagulate command or automatic shut down. If no command is selected, the output signal from NOR gate 1494 remains high.

The output signal from NOR gate 1494 is coupled through inverter 1495, resistor 3412 and potentiometer 3908 to ground. The wiper of potentiometer 3908 is connected through capacitor 4415 to one input of operational amplifier 1497, which input is connected to ground through capacitor 4416. The junction between capacitors 4415 and 4416 is coupled to the second input of amplifier 1497 through capacitor 4414. The output from operational amplifier 1497 is coupled to speaker 9906 through capacitor 4417. The other side of the speaker is connected to circuit ground. Speaker 9906 produces an audible tone to indicate the generator status, the volume of the tone being adjustable by means of potentiometer 3908.

Figure 3:
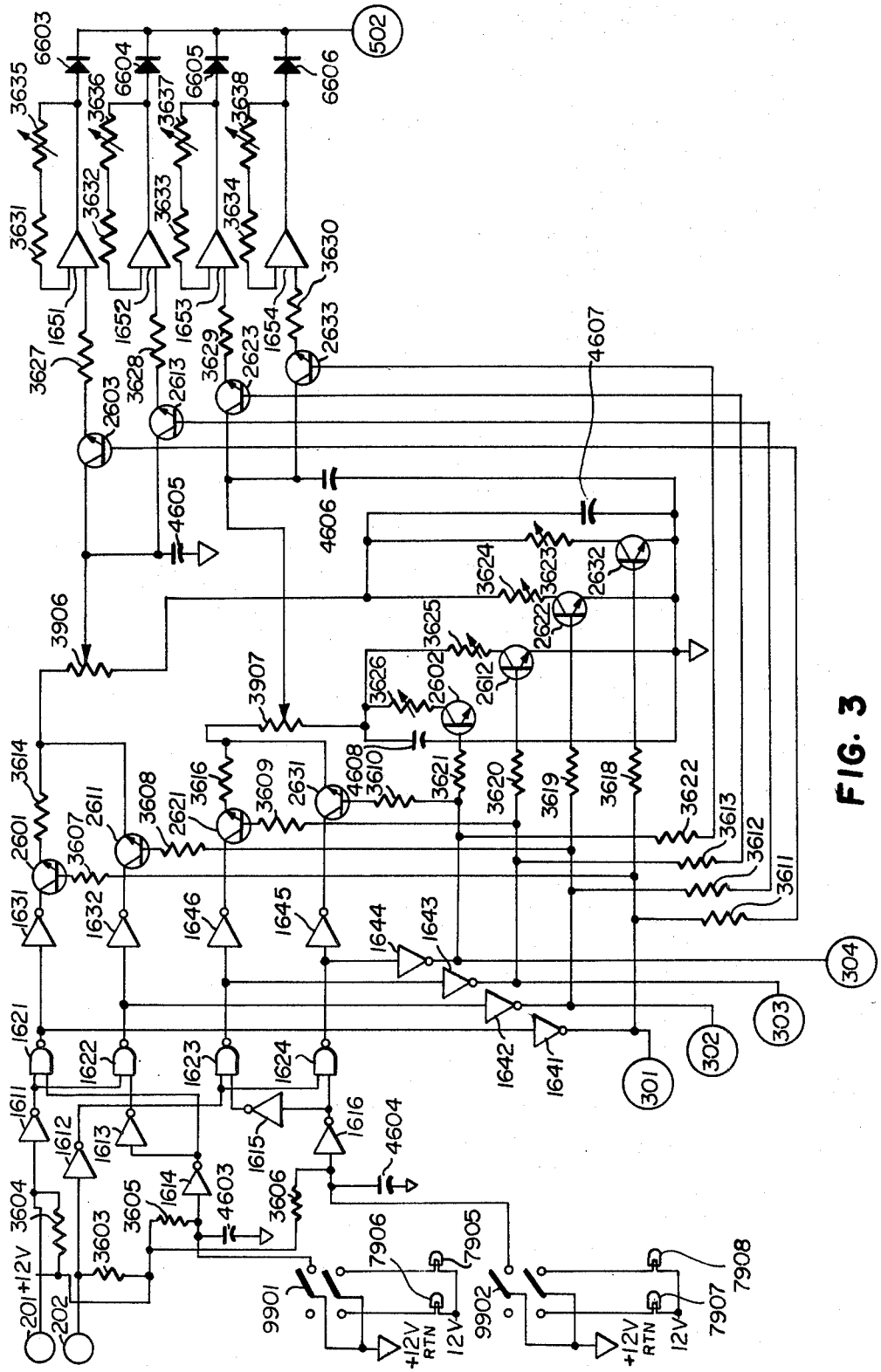
FIG. 3 is a schematic circuit diagram of the mode control unit 105 and output control amplifiers 107, 109, 111 and 113 of FIG. 1.

The circuit of FIG. 3 is the mode control unit 105 and amplifiers 107, 109, 111 and 113 of FIG. 1. Command line 201 is coupled to the input terminal of inverter 1611. Additionally, a 12 volt source is connected through resistor 3604 to the input terminal of inverter 1611 so that this input terminal is normally high. The output of inverter 1611 is coupled to input terminals of NAND gates 1621 and 1622. When command line 201 is activated, the treating physician may select between a pure cut or blend mode by means of the double pole/double throw switch 9901. Both wiper arms of switch 9901 are grounded. A 12 volt supply is connected through lamps 7905 and 7906 to respective contacts for one pole of switch 9901. Of the remaining two contacts for the second pole of switch 9901, one is coupled to the input of inverter 1614, and from that point through capacitor 4603 to ground. The output signal from inverter 1614 is coupled to an input of NAND gate 1621 and is also coupled to the input of inverter 1613. The output signal from inverter 1613 is coupled to an input of NAND gate 1622.

When command line 201 is activated (as represented by a low level signal) and one wiper arm of switch 9901 makes contact with lamp 7905, the output signal from NAND GATE 1621 goes low and the output of NAND gate 1622 goes high. Lamp 7905 is actuated thereby to indicate that a pure cut mode has been selected. When command line 201 is low and switch 9901 makes contact with lamp 7906, the output signal from NAND gate 1621 is high and the output signal of NAND gate 1622 is low. Under such circumstances, lamp 7906 is lit to provide a visual indication that the blend mode of operation has been selected.

Similarly, when command line 202 is activated, the treating physician may select between the desiccate and fulgurate operation modes by means of double pole/double throw switch 9902. Both wiper arms of switch 9902 are grounded. A 12 volt supply is connected through lamps 7907 and 7908 to the respective contacts for one pole of switch 9902. Of the remaining two contacts of the other pole of switch 9902, one contact is coupled to the inverter 1616 and the other contact remains unconnected. A 12 volt supply is also coupled through resistor 3606 to the input terminal of inverter 1616, and from that point through capacitor 4604 to ground. The output signal from inverter 1616 is coupled to an input terminal of NAND gate 1624 and also to the input terminal of inverter 1615. The output signal from inverter 1615 is coupled to the input of NAND gate 1623.

When command line 202 is activated (i.e. at a low level) and one wiper arm of switch 9902 makes contact with lamp 7907, the output signal from NAND gate 1623 is low and the output signal from NAND gate 1624 is high. Also, current is drawn through lamp 7907, thereby indicating that the desiccate mode of operation has been selected. When command line 202 is low and switch 9901 makes contact with lamp 7908, the output signal from NAND gate 1623 is high and the output signal from NAND gate 1624 is low. In addition, lamp 7908 is lit, thereby providing a visual indication that the fulgurate mode of operation has been selected.

Amplifier 109, which operates during the blend mode, may be considered typical of amplifiers 107, 109, 111 and 113 and can be described as follows. The output signal from NAND gate 1622 is connected to the input terminal of inverter 1632. The output signal from inverter 1632 is connected to the collector of NPN transistor 2611. The output signal from NAND gate 1622 is also coupled to an input terminal of inverter 1642 which supplies base current to the three transistors 2611, 2613, and 2622 associated with the blend mode amplifier 109. The output signal from inverter 1642 is coupled through resistor 3612 to the base of NPN transistor 2613. Transistors 2611, 2622 and 2613 operate in their switching mode; that is, when the output of inverter 1642 is high and current is supplied through the base resistors of the transistors, the collector-emitter path of each transistor conducts in saturation mode. When no base current is supplied, the collector-emitter path is open. The output signal from inverter 1642 also drives mode line 302.

The emitter of transistor 2611 is connected to one side of potentiometer 3906, the other side of which is connected to resistor 3624 and one side of capacitor 4607. The other side of capacitor 4607 is connected to ground. Resistor 3624 is a variable resistor connected to the collector of transistor 2622, the emitter of which is connected to ground. The wiper arm of potentiometer 3906 is coupled through capacitor 4605 to ground and to the collector of transistor 2613. The emitter of transistor 2613 is connected through resistor 3628 to the non-inverting input terminal of operational amplifier 1652.

When the output signal from NAND gate 1622 is low, thereby indicating that the blend mode of operation is in progress, the output signal from inverter 1632 is high. This voltage is connected through the collector-emitter path of transistor 2611 to potentiometer 3906. The voltage across this potentiometer is established by the difference between the voltage supplied by inverter 1632 and the voltage across variable resistor 3624 and the collector-emitter circuit of transistor 2622. In effect, variable resistor 3624 sets the minimum value of the output power range which may be controlled by potentiometer 3906.

The output signal from operational amplifier 1652 is connected in negative feedback relationship through potentiometer 3636 and resistor 3632 to the inverting input terminal of operational amplifier 1652. This feedback loop establishes the gain of the operational amplifier so that, in effect, the variable resistor 3636 establishes the maximum limit of the output power range controlled by the setting of potentiometer 3906. The output signal from operational amplifier 1652 is also connected through diode 6604 to the voltage controlled main amplifier 200 via signal line 502. The output of operational amplifier 1652 easily overcomes the forward bias voltage of diode 6604; however, the reverse bias voltage of diode 6604 prevents any of the other three amplifiers 1651, 1653, 1654 that are coupled to line 502 from feeding their output signals into the circuit of operational amplifier 1652.

The amplifiers 107, 111 and 113 for the other modes of operation operate in a similar fashion wherein: transistors 2601, 2603 and 2632 and operational amplifier 1651 form part of the circuit for amplifier 107; transistors 2621, 2623 and 2612 and operational amplifier 1653 form part of the circuit for amplifier 111; and transistors 2631, 2602 and 2633 and operational amplifier 1654 form part of the circuit for amplifier 113.

Figure 4:
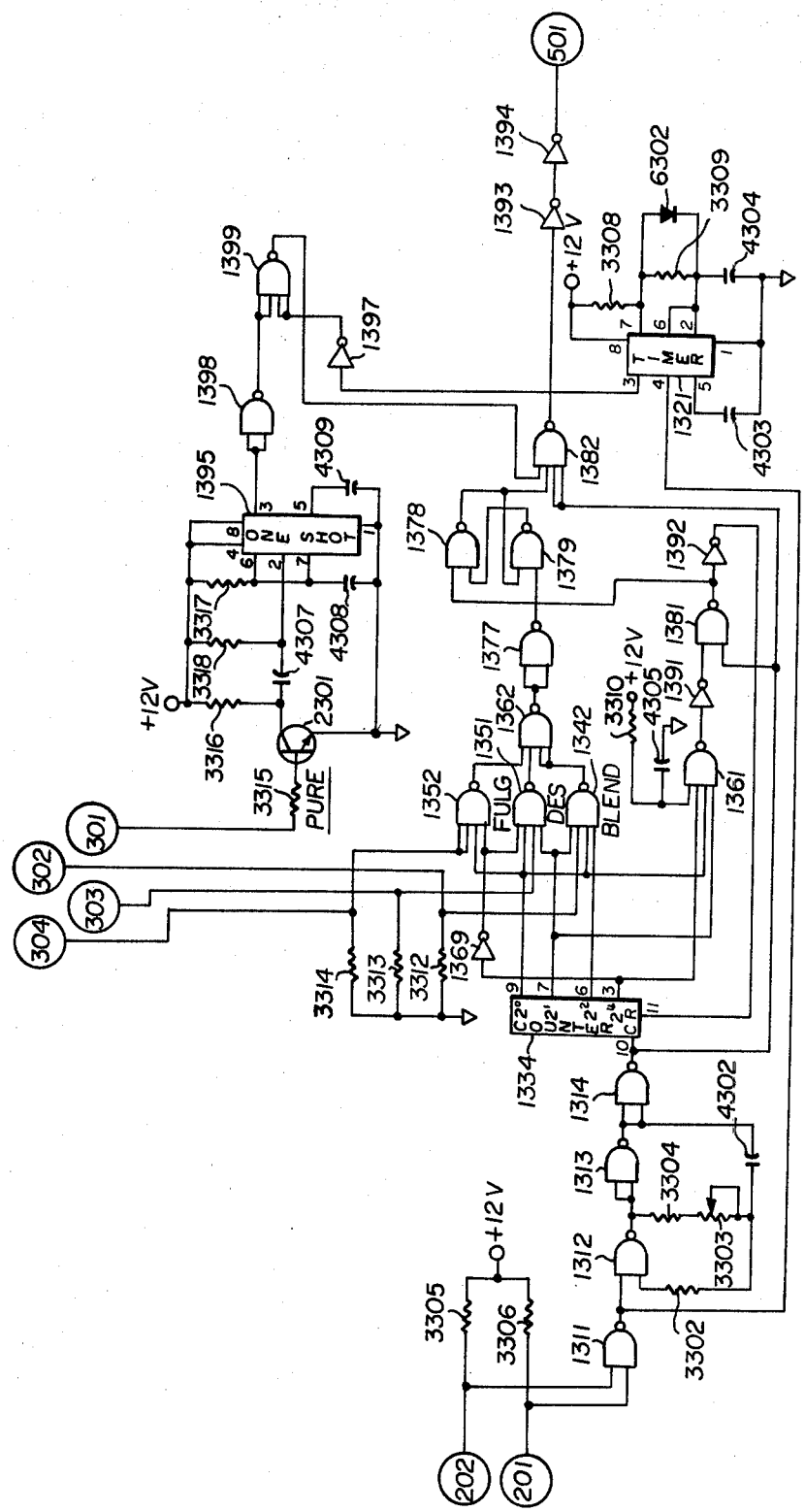
FIG. 4 is a schematic circuit diagram of the high frequency oscillator 115, timer 117, one-shot 1395, variable frequency divider 119, OR gate 1399 and NAND gates 1311 and 1382 of FIG. 1.

Specific reference is now made to FIG. 4 which illustrates the detailed circuitry for the high frequency oscillator 115, the variable high frequency divider 119, the low frequency oscillator/timer 117, the one-shot multivibrator 1395, and NAND gates 1311 and 1382.

Command line 201 is connected to one input of two-input NAND gate 1311. A 12 volt supply is also connected, through resistor 3306, to that input of NAND gate 1311 so that when command line 201 is not activated, the input is high. Command line 202 is connected to another input of NAND gate 1311 and the 12 volt supply is also connected through resistor 3305 to this second input of that gate. Therefore, when command line 202 is not activated, the second input is high. However, is either command line is activated, the output of NAND gate 1311 goes low, thereby activating the fixed high frequency oscillator 115 (elements 1312, 1313, 3302-3304; 4302) and the low frequency oscillator 117 (elements 1321, 3308, 3309, 4303 and 4304).

The output signal from NAND gate 1311 is connected to one input of NAND gate 1312. The output signal from NAND gate 1312 is coupled to the input of NAND gate 1313 connected as an inverter. The output signal from inverter 1313 is, in turn, coupled as a feedback signal through capacitor 4302 and resistor 3302, in series, to the second input of NAND gate 1312. The output of NAND gate 1312 is also coupled as a feedback signal through resistor 3304 and potentiometer 3303 in series to the junction between resistor 3302 and capacitor 4302. These elements comprise the fixed high frequency oscillator 115, the frequency of which is initially calibrated and set by adjustment of potentiometer 3303. The output signal from the oscillator is the output signal of inverter 1313 which is coupled to the input terminal of NAND gate 1314 connected as an inverter. The output signal from inverter 1314 is coupled to the count input of binary counter 1334, to one input of NAND gate 1381, and to two of the four inputs of NAND gate 1382.

The output signal from NAND gate 1311 is also coupled to the trigger input at pin 4 of timer 1321 which is preferably an intergrated circuit type 555 timer. The circuit associated with timer 1321 corresponds to timer 117 of FIG. 1. A 12 volt supply is connected directly to pin 8 of timer 1321 and through resistor 3308 to pin 7 of that timer. Pin 7 is also resistively coupled to pin 2 through resistor 3309, with pin 2 being directly connected to pin 6. Pin 2 is also capacitively coupled to ground by means of capacitor 4304. Pin 1 is directly coupled to ground and pin 5 is capacitively coupled to ground via capacitor 4303. The output terminal of the low frequency oscillator/timer 117 corresponds to pin 3 of timer 1321 and is connected to the input terminal of inverter 1397. The output signal from inverter 1397 is connected as one input signal for NAND gate 1399. The other input signal for NAND gate 1399 is derived from NAND gate 1398 connected as an inverter which, in turn, receives its output signal from pin 3 of one-shot multivibrator 1395. One-shot multivibrator 1395 is preferably an integrated circuit timer type 555 which has its pins 4 and 8 directly coupled to the 12 volt supply and its pins 6 and 7 resistively coupled to the 12 volt supply through resistor 3317. Pins 5 and 7 are capacitively coupled to ground through capacitors 4309 and 4308, respectively. Pin 1 is directly connected to ground. The input or trigger terminal for one-shot multivibrator 1395 is pin 2 which receives its signal from the collector of NPN transistor 2301 through series capacitor 4307. Pin 2 is also resistively coupled to the 12 volt supply through resistor 3318. The collector of transistor 2301 is coupled to the 12 volt supply through resistor 3316 and the emitter of the transistor is grounded. The trigger signal for transistor 2301 is derived from the pure cut mode signal line 301 via series resistor 3315 at the base of transistor 2301.

One-shot multivibrator 1395 is triggered by the onset of a pure cut command signal applied to the base of transistor 2301. The pure cut command signal causes transistor 2301 to conduct, thereby producing a low voltage at pin 2 of one-shot multivibrator 1395. A 360 millisecond gating pulse is provided from output pin 3 to NAND gate 1399 via inverter 1398. During the interval that the 360 millisecond gating pulse is present, the output signal from NAND gate 1399 remains high thereby preventing the low frequency secondary modulation signal, which is provided by timer 1321, from affecting the state of the output signal of NAND gate 1399. The output signal from NAND gate 1399 is provided as one of the input signals to NAND gate 1382 which, as described above, also receives the high frequency signal from inverter 1314. Ignoring the third input signal to NAND gate 1382 for the moment, it may be seen that the 360 millisecond gating pulse from one-shot multivibrator 1395 acts through NAND gate 1399 to continuously permit the high frequency signal to pass NAND gate 1382 without any effect from the secondary modulation signal produced by timer 1321. Upon expiration of the 360 millisecond initial gating period, the output signal from NAND gate 1399 alternates between high and low states in accordance with the frequency and duty cycle of the secondary modulation signal provided by timer 1321. Therefore, in the pure cut mode, there is an initial period during which unmodulated high frequency cutting signal is passed continuously through NAND 1382 and series-connected inverters 1393 and 1394 to signal line 501. After the initial start up period, the high frequency signal continues to be modulated in the steady state by the secondary modulation signal. The amplitude of the high frequency cutting signal does not change from the initial start up interval to the steady state condition; however, the energy level during the start up interval is considerably higher due to the continuous, unmodulated nature of the signal passed through NAND gate 1382.

Counter 1334 is preferably an integrated circuit type counter 4040. The state of the binary signals at output pins 9, 7, 6 and 3 is a binary representation of the count of pulses from the high frequency oscillator 115 applied at the count terminal at pin 10. The three NAND gates 1342, 1351 and 1352 respond to the count in counter 34 to vary the primary modulation control function in accordance with the mode selected by the operator as represented by the active line of mode control lines 302, 303 and 304. The input signal applied to inverter 1369 is derived from pin 3 of counter 1334. The input signals for NAND gate 1342 are derived from the mode line 302 and pins 6, 7 and 9 of counter 1334. The input signals for NAND gate 1351 are derived from mode line 303, inverter 1369 and pins 7 and 9 of counter 1334. The input signals for NAND gate 1352 are derived from mode line 304, inverter 1369 and pin 9 of counter 1334. The output signals from each of these three NAND gates 1342, 1351 and 1352 are connected as inputs to NAND gate 1362, the output of which is applied to NAND gate 1377 connected as an inverter.

A set-reset flip-flop is formed by NAND gates 1378 and 1379. Specifically, the output signal from NAND gate 1378 is coupled to one input of NAND gate 1379, and the output of NAND gate 1379 is coupled to one input of NAND gate 1378. The output signal from inverter 1377 is connected to the second input of NAND gate 1379, while the second input of NAND gate 1378 receives its signal from the output terminal of NAND gate 1381. The output signal from NAND gate 1378 is connected as a third input signal to NAND gate 1382 to control the modulated signal passing through that gate. In the pure cut mode, the output signal from NAND gate 1378 remains high so that it has no effect in inhibiting the unmodulated rapid start condition or the modulated steady state condition in the pure cut mode. Counter 1384, therefore, has no effect on the pure cut mode.

A further NAND gate 1361 receives three input signals from pins 3, 7 and 9 of counter 1334, respectively. A fourth input for NAND gate 1361 is coupled to the junction between a resistor 3310 and a capacitor 4305. The other side of the capacitor 4305 is connected to ground whereas the other side of resistor 3310 is connected to the 12 volt supply. The output signal of NAND gate 1361 is connected to the input of inverter 1391 which drives one input of NAND gate 1381. The other input terminal of NAND gate 1381 receives a signal from the output terminal of inverter 1314. NAND gate 1381 provides its output signal to the input of an inverter 1392 which is coupled to the reset terminal at pin 11 of counter 1334.

Counter 1334, NAND gates 1378, 1379 and their associated circuit elements, comprise the variable high frequency divider 119. When the high frequency oscillator is operating under the control of command lines 201 or 202, counter 1334 counts the oscillation cycles of the high frequency signal until NAND gate 1381 provides a low output level which resets the counter through inverter 1392. This occurs when pins 3, 7 and 9 of counter 1334 are all high and the output of inverter 1314 is low. This corresponds to a binary count of 10011 which represents a decimal equivalent of the number nineteen. Therefore, counter 1334 recycles to 00000 upon reaching count 10011 so that each counting cycle is twenty counts long.

Pulses or cycles from the high frequency oscillator 115 pass through NAND gate 1382 and inverters 1393 and 1394 to the main voltage controlled amplifier 200 via line 501 whenever the output signal from NAND gate 1378 and the output signal from NAND gate 1399 are high. The output signal from NAND gate 1378 is triggered to a high level when the output signal from inverter 1377 is high. The latter signal is high during each cycle of counter 34 until an output pulse group is selected by one of NAND gates 1342, 1351 and 1352.

In the pure cut mode, none of NAND gates 1342, 1351 or 1352 is actuated because lines 302, 303 and 304 are not actuated. The signal provided by inverter 1377 is therefore high so that flip-flop 1378, 1379 remains reset from the previous reset pulse from NAND gate 1381 at the start of the count cycle at counter 1334. The output signal from NAND gate 1378 is therefore high and permits NAND gate 1382 to pass the high frequency signal from NAND gate 1314 solely under the control of NAND gate 1399. As described above, the output signal from NAND gate 1399 remains high for a period of approximately 360 milliseconds after the onset of the pure cut mode. With reference to FIG. 8, during this 360 millisecond interval, the high frequency cutting signal is permitted to pass without interruption through NAND gate 1382. Upon termination of the 360 millisecond start up interval, the secondary modulation takes over, resulting in alternating intervals of inhibited passage of the high frequency signal followed by passage of the high frequency signal. As illustrated in FIG. 8, the secondary modulation period is four milliseconds long with a duty cycle of 60%. In other words, the high frequency signal passes through NAND gate 1382 for 2.5 milliseconds and is inhibited for 1.5 milliseconds. The amplitude and frequency of the high frequency cutting signal remain the same in both the start up period and the steady state period; the only difference resides in the duty cycle which is 100% during the start up period and 60% during the steady state period.

In the blend mode, blend mode line 302 activates NAND gate 1342 which resets the output of NAND gate 1378 at count seven during the twenty-count cycle of counter 1334. The signals passed through NAND gate 1382 in the blend mode may, therefore, be represented as illustrated in FIG. 9 wherein the primary modulation comprises a duty cycle of seven counts on and thirteen counts off. It is to be understood that the plot in FIG. 9 represents the primary modulation only and that the secondary modulation, which is at a frequency of 250 Hz, is also present in the overall blend signal passed by NAND gate 1382. In this respect, it will be understood that the secondary modulation provides a 2.5 millisecond on period during which the high frequency signal is passed in seven-count bursts and inhibited in alternating thirteen-count intervals. These 2.5 millisecond periods are interlaced with 1.5 millisecond periods wherein no high frequency signal is passed through NAND gate 1382.

In the desiccate mode, the desiccate command signal on line 303 activates NAND gate 1351. This NAND gate resets the output of NAND gate 1378 after three counts of the twenty-count cycle of counter 1334. The resulting primary modulation effect for the desiccate mode is illustrated in FIG. 10 wherein three counts of the high frequency signal are passed and seventeen are blocking during each twenty-count cycle of counter 1334. Again, it must be remembered that the 250 Hz secondary modulation signal permits passage of the high frequency signal only in alternate 2.5 millisecond intervals and entirely blocks any passage of the high frequency signal in alternate 1.5 millisecond intervals.

Figure 12:
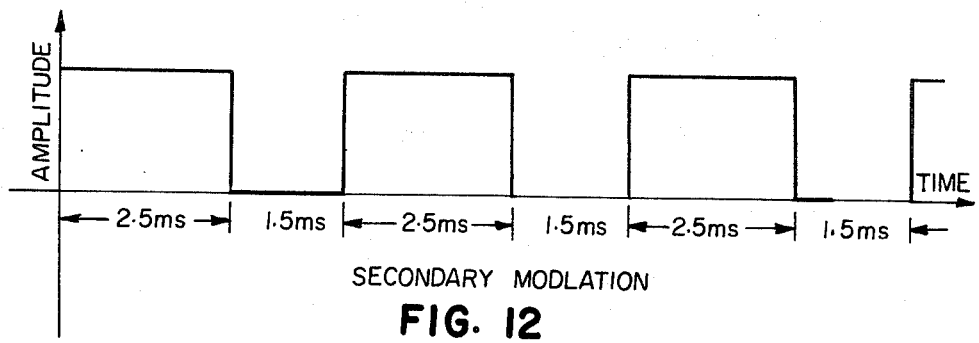
FIG. 12 is a plot of amplitude versus time of the secondary modulation wave form generated by timer unit 117 of FIG. 1.

The fulgurate mode is characterized by the signal on line 304 activating NAND gate 1352 which resets the output signal from NAND gate 1378 after a single count. This output of NAND gate 1378 remains low for the remaining nineteen pulses of the twnety-count cycle of counter 1334. This primary modulation portion of the fulgurate mode is illustrated in FIG. 11. Once again, it is to be remembered that the secondary modulation signal permits the fulgurate mode signal to pass only during alternate 2.5 millisecond intervals of the secondary modulation wave form. In this regard, referring to FIG. 12, the secondary modulation wave form may be seen to have a period of 4 milliseconds with a duty cycle of 60%. In other words, the secondary modulation permits passage of the high frequency signal for the 2.5 milliseconds during which the wave form in FIG. 12 is high and inhibits passage of the high frequency cutting signal during the 1.5 milliseconds when the secondary modulation wave form is low.

Referring specifically to FIG. 5 of the accompanying drawings, the voltage-controlled main amplifier 200 of FIG. 1 is illustrated in detail. An NPN transistor 2201 has its collector coupled to the 12 volt supply through series-connected resistors 3212 and 3206. The emitter of transistor 2201 is connected directly to ground. Resistores 3212, 3201, 3203 and 3204 are connected in series between the 12 volt supply and its return path and serve as a voltage divider for establishing a bias voltage for the base of transistor 2201 at the junction between resistors 3203 and 3204. A parallel circuit including capacitor 4201 and zener diode 6201 is connected between resistor 3212 and the 12 volt return path.

The output signal from NAND gate 1382 in FIG. 4 is passed through inverters 1393 and 1394 of FIG. 4 to line 501 which is received in the circuit of FIG. 5 and passed through capacitor 4202 and resistor 3203, in series, to the base of transistor 2201. Capacitor 4202 serves to block spurious d.c. level variations from reaching the base of transistor 2201 and passing through the main amplifier circuit 200 to the patient.

The output signals from amplifiers 107, 109, 111 and 113, which are illustrated in detail in the circuit of FIG. 3, are applied to the circuit of FIG. 5 on line 502 which is connected to resistor 3639. The signals are passed through this resistor to the base of NPN transistor 2604. The base of transistor 2604 is coupled to the thirty volt return path through the parallel circuit comprising capacitor 4609 and resistor 3640. The collector of transistor 2604 is coupled to the thirty volt return path through the parallel circuit comprising zener diode 6601 and capacitor 4601. The thirty volt supply is resistively coupled to the collector of transistor 2604 through resistor 3601.

The collector of transistor 2201 is connected through resistor 3207 to the base of NPN transistor 2202. The base and emitter of transistor 2202 are resistively coupled to the 30 volt return path through resistor 3208 and resistor 3209, respectively. The emitter of transistor 2604 is coupled through resistor 3213 to the parallel circuit comprising resistor 3202 and capacitor 4203 which is returned to the thirty volt return path. The emitter of transistor 2604 is also connected through resistor 3213 to a parallel circuit comprising capacitor 4204, resistor 3205 and the primary winding of isolation transformer 5201, the other side of this parallel circuit being connected to the collector of transistor 2202. Capacitor 4204, resistor 3205 and transformer 5201 form a parallel resonant circuit which produces the drive signal for the inductively coupled following stage comprising NPN transistor 2905. The secondary winding of transformer 5201 is connected across the base-emitter junction of transistor 2905 which has its collector coupled through the primary winding of transformer 5202 to the +180 volt supply. The emitter of transistor 2905 and one side of the secondary winding of transformer 5202 are directly connected to the 180 volt return path. The other side of the secondary winding of transformer 5202 is connected through resistor 3211 to a constant current amplifier stage in the voltage-controlled main amplifier 200. This constant current amplifier stage includes four parallel-connected NPN transistors 2901, 2902, 2903 and 2904. The collectors of these transistors are connected together as are their base electrodes which are also connected to the side of resistor 3211 opposite the secondary winding of transformer 5202. The emitters of the four transistors are connected to one side of respective resistors 3901, 3902, 3903, 3904, the other sides of which are connected together.

The signal obtained from the secondary winding of transformer 5202 drives each of transistors 2901, 2902, 2903 and 2904 and is derived from the "flyback mode" or the stored energy in the inductance of transformer 5202. Therefore, the last pulse in the pulse group of the high frequency signal is free to ring and thereby provide a large peak drive signal. This amounts to a voltage spike which saturates transistors 2901, 2902, 2903 and 2904. This last pulse voltage spike for each group of high frequency pulses passed from the circuit of FIG. 4 may be seen in each of the high frequency bursts illustrated in FIGS. 8, 9, 10 and 11.

Figure 15:
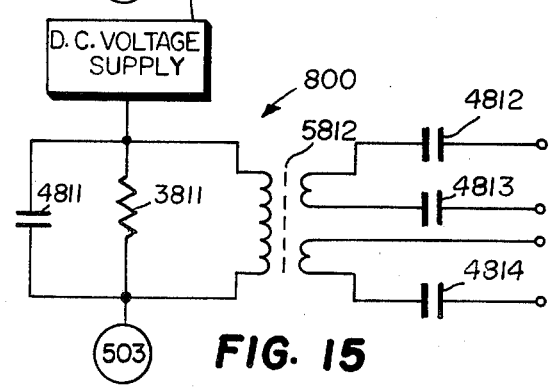
FIG. 15 is a schematic circuit diagram for an alternative patient isolation unit for the electrosurgical generator of the present invention.

The output signal from the constant current amplifier stage is provided at the collectors of transistors 2901, 2902, 2903 and 2904 on signal line 503 which is passed to the isolation unit 800 of FIG. 1. One such isolation unit is illustrated in FIG. 15 and includes a tank circuit comprised of capacitor 4811, resistor 3811 and the primary winding of a transformer 5812. These parallel-connected elements form a resonant circuit, the resonance being at a frequency which is tuned to a lower frequency than the 475 KHz of the high frequency signal generated at high frequency oscillator 115. The other side of the tank circuit is coupled to the d.c. voltage supply 123 which is at +180 volts. By tuning the tank circuit to a frequency lower than the high frequency signal, the amplitude of all of the pulses in each pulse burst is limited with the exception of the final pulse which is free to ring out to its maximum peak amplitude. The positive output signals of the unit are derived from the flyback mode of operation of transformer 5812. Therefore, the last pulse derived from the "flyback" configuration of transformer 5202, which in turn saturates transistors 2901, 2902, 2903 and 2904, together with the flyback-connected output from transformer 5812, results in a very high voltage spike. This spike achieves a high ratio of peak power to rms, which ratio is generally designated as the crest factor ratio. A high crest factor ratio is desirable as an efficient cause of ionization in the cutting signal without excessive tissue heating.

Figure 14:
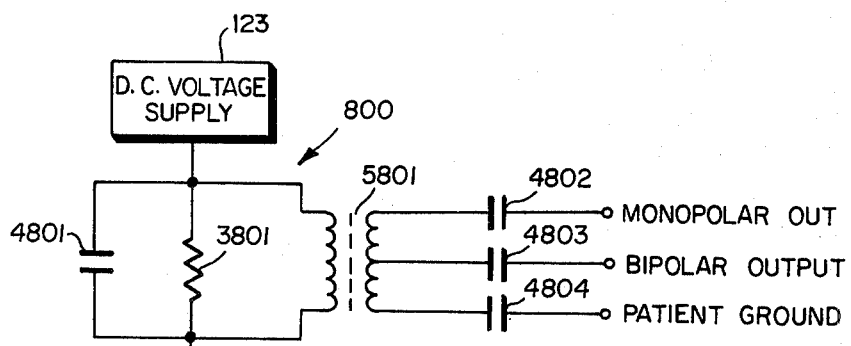
FIG. 14 is a schematic circuit diagram of a patient isolation unit employed for the electrosurgical generator of the present invention.

Another embodiment of isolation unit 800 is illustrated in FIG. 14. The primary winding of transformer 5801 is connected in parallel with resistor 3801 and capacitor 4801 to form a resonant tank circuit. Signal line 503 is connected to one side of the tank circuit and the d.c. voltage supply 123 is connected to the other side. One side tap of the secondary winding of transformer 5801 is connected through capacitor 4802 to the monopolar output terminal of the electrosurgical generator. Another side tap is connected through capacitor 4804 to the patient return terminal of the electrosurgical generator. The center tap of the secondary windong of transformer 5801 is connected through capacitor 4803 to the bipolar output terminal of the generator.

The isolator unit of FIG. 15 has two secondary windings for transformer 5812 as opposed to the single center tapped secondary winding for transformer 5801 of FIG. 14. The side taps of one secondary winding of transformer 5812 are connected through capacitors 4812 and 4813 to active and dispersive monopolar output terminals, respectively. The other secondary winding of transformer 5812 has one side tap coupled through capacitor 4814 to one bipolar output terminal and has another side tap connected directly to the other bipolar output terminal.

The circuit illustrated in FIG. 6 is a display device for digitally displaying the output level of the electrosurgical generator of the present invention. In the preferred embodiment of the invention, two such display units are provided, one for each of the two command groups (i.e. cut and coagulate). A potentiometer 3909 from the first display device is ganged to potentiometer 3906, which is illustrated in FIGS. 1 and 3 and which serves the cut command group. A similar potentiometer 3909 of the second display device (not illustrated) is ganged to potentiometer 3907, which is illustrated in FIGS. 1 and 3 and serves the coagulate command group.

A five volt supply is connected through resistors 3701 and 3702 and through variable resistor 3703, all connected in series, to one side of potentiometer 3909. The other side of potentiometer 3909 is connected to the five volt return bus. The wiper arm of potentiometer 3909 is connected through a resistor 3706 to pin 11 of an analog-to-digital converter 1700. This analog-to-digital converter is preferably an integrated circuit type ADD3501. The five volt supply is also connected through resistor 3701 to pins 1 and 9 of the analog-to-digital converter 1700. Pins 1 and 9 are resistively coupled to pin 18 through resistor 3704. Pin 18 is also resistively coupled to the five volt return path via resistor 3705. A parallel circuit comprising capacitor 4701 and diode 6701 is connected between the five volt return path and the junction between resistors 3701 and 3704. Pins 2 and 19 are capacitively coupled to the five volt return path by means of capacitors 4702 and 4703, respectively. Pins 19 and 20 are resistively coupled by means of resistor 3707. Pin 11 and pin 14 are capacitively coupled to the five volt return path by means of capacitors 4704 and 4705, respectively. Pin 15 is directly coupled to the five volt return path. Resistor 3708 is connected between pins 14 and 17, and resistor 3709 is connected between pins 17 and 16. Pin 25 is coupled directly to the five volt return path.

The output signals from the analog-to-digital converter 1700 are pins 6, 5, 4, 3, 28, 27 and 26. These pins are connected through a resistor pack 3710 to the segment pins of the 7-segment displays 1703 and 1704 which are connected in parallel. Pin 23 of the analog-to-digital converter is connected to inverter 1701 which drives the drive terminal of display 1703. Pin 22 of the analog-to-digital converter is connected to the input of inverter 1702 which drives the drive connection of display 1704. By means of the circuit described above, the setting of the potentiometer 3909, as reflected by the voltage appearing on its wiper arm, is converted to a digital display at display units 1703 and 1704.

Figure 13:
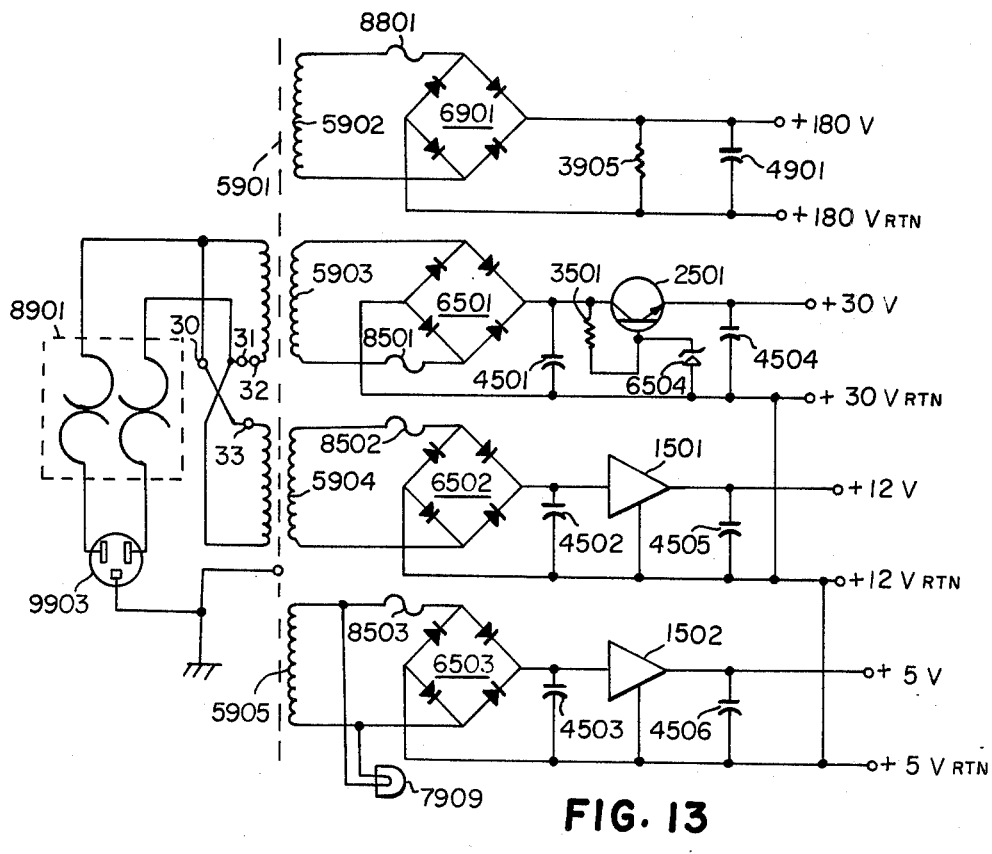
FIG. 13 is a schematic circuit diagram of a power supply employed for the electrosurgical generator of the present invention.

The circuit of FIG. 13 is a power supply for the electrosurgical generator of the present invention. Primary power for the power supply is standard 110 volts, 60 1 Hz power supplied through a standard three-wire plug 9903 The ground pin of plug 9903 is connected directly to the core of a power distribution transformer 5901. The two power pins of plug 9903 are connected through the dual-pole circuit breaker 8901 to the side taps of the primary winding of transformer 5901. The primary winding is shown in a form suitable for accepting a 110-volt input; however, it may be rewired to accept 220 volts by breaking the connections at points 30 and 31 and making a connection between points 32 and 33.

Transformer 5901 has four secondary windings 5902, 5903, 5904 and 5905. One side tap of secondary winding 5902 is coupled directly to one input terminal of a full-wave bridge rectifier 6901; the other side tap of winding 5902 is coupled through fuse 8801 to the second input of bridge 6901. A parallel circuit comprising resistor 3905 and capacitor 4901 is connected across the output terminal of the bridge 6901 and the +180 volt supply and 180 volt return line are connected to opposite sides of the parallel circuit.

Secondary winding 5903 provides the 30 volt supply voltage. Specifically, full-wave bridge rectifier 6501 has its input terminals connected across secondary winding 5903 with fuse 8501 being connected between the bridge and one side of the secondary winding. A capacitor 4501 is connected directly across the output terminals of the bridge 6501. The positive output terminal of the bridge is connected to the collector of an NPN transistor 2501 which is resistively coupled to the base of that transistor by resistor 3501. A zener diode 6504 is connected between the base of transistor 2501 and the negative output of bridge 6501. The emitter of transistor 2501 provides the +30 volt output for the circuit. A capacitor 4504 is connected between the emitter of transistor 2501 and the negative output terminal of bridge 6501 which serves as the +30 volt return line.

Second winding 5904 provides the +12 volt supply voltage for the system. A full-wave bridge rectifier 6502 is connected across the winding 5904 and is protected by fuse 8502. Capacitor 4502 is connected across the output terminal of bridge 6502. A voltage regulator 1501 is driven from the positive output terminal of bridge 6502. The ground reference terminal of voltage regulator 1501 is connected to the negative output terminal of bridge 6502. The output signal from the voltage regulator 1501 provides the +12 volt supply voltage for the system and is filtered by capacitor 4505 which is connected across the output terminal of the regulator and the negative output terminal of bridge 6502, the latter serving as the +12 volt return line. The +12 volt return line is connected directly to the +30 volt return line and to the +5 volt return line to serve as a circuit ground.

Secondary winding 5905 is associated with the +5 volt supply voltage circuitry. A full-wave bridge rectifier 6503 is connected across winding 5905 and is protected by fuse 8503. A capacitor 4503 is connected across the output terminals of bridge 6503. Voltage regulator 1502 is driven by the positive output terminal of bridge 6503 and has its ground reference terminal connected to the negative output terminal of bridge 6503. The output terminal from voltage regulator 1502 provides the system five volt supply which is filtered by capacitor 4506 connected across the output terminal of voltage regulator 1502 and the negative output terminal of bridge 6503. The negative output terminal of bridge 6503 serves as the five volt return line.

A lamp 7909 is connected directly across secondary winding 5905 to serve as an indication that primary power is supplied to the system.

The isolator units 800 illustrated in FIGS. 14 and 15 are arranged to provide an output impedance which is greater than 1000 Ohms in order to provide impedance-matching for the high-impedance tissue of a joint on which surgery is to be performed. This impedance-matching is achieved by providing an appropriate turns ratio between the primary and secondary windings of transformer 8501 or transformer 5812 in order to achieve the desired impedance. As noted above, clinical evaluations have revealed that the electrical impedance presented by joints of the human body (for example, the knee when subjected to arthroscopic procedures) is on the order to 1,000 Ohms or greater. On this basis, transformer 5801 or transformer 5812 is provided with a turns ratio selected to match this impedance in order to achieve optimal power transfer efficiency from the electrosurgical generator to the surgical site.

The table set forth below provides a listing of specific parameters and components which may be utilized with the element described and illustrated in the preferred embodiment. It should be noted, however, that the list of components is for purposes of example only and that the scope of the invention shall not be limited thereto.

TABLE

Integrated Circuits:
Type 4023 three-input NAND gates: 1461, 1462, 1481 and 1483.
Type 4012 quad-input NAND gates: 1342, 1351, 1352, 1361, 1362, 1381, 1382 and 1399.

TABLE-continued

Type 4049 inverters: 1369, 1391, 1392, 1393, 1394, 1397, 1431, 1432, 1433, 1434, 1435, 1436, 1471, 1472, 1473, 1482, 1495, 1611, 1612, 1613, 1614, 1615, 1616, 1631, 1632, 1641, 1642, 1643, 1644, 1645 and 1646.
Type 4011 NAND gates: 1311, 1312, 1313, 1314, 1377, 1378, 1379, 1399, 1621, 1622, 1623 and 1624.
Type 4001 NOR gates: 1441, 1442, 1443, 1444, 1451, 1452, 1453, 1491, 1492 and 1493.
Type 555 timers: 1321 and 1395.
Type 556 timers: 1411 and 1412.
Type 4N28 opto-isolators: 1421 and 1422.
Type 4025 three-input NOR gate: 1494.
Type 4040 binary counters: 1334 and 1496.
Type 3900 operational amplifiers: 1651, 1652, 1653 and 1654.
Type 380N audio amplifier: 1497.
Type 75492 inverters: 1701 and 1702.
Type ADD 3501 analog-to-digital converter: 1700
7-segment displays: 1703 and 1704.
Type LM340T12 voltage regulator: 1501.
Type LM340T5 voltage regulator: 1502.

Capacitors:

10 μF, 35 v: 4201, 4409, 4417 and 4702.
.1 μF, 50 v: 4202, 4415, 4416, 4603, 4604, 4605, 4606, 4607, 4608 and 4609.
50 μF, 50 v: 4203, 4505 and 4506.
200 pF, 500 v: 4204.
.01 μF, 100 v: 4303, 4304, 4309, 4403, 4404, 4405, 4406, 4407, 4408, 4410, 4411, 4412, 4413, 4420 and 4421.
100 pF, 200 v: 4302.
.001 μF, 200 v: 4307 and 4414.
47 μF, 20 v: 4701.
220 pF, 200 v: 4703.
.47 μF, 35 v: 4704 and 4705.
22000 pF, 500 v: 4801.
12000 pF, 500 v: 4811.
.01 μF, 3000 v: 4802, 4083 and 4804.
500 mF; 4901.
10 μF, 50 v: 4601.
150 μF, 50 v: 4501.
1 μF, 35 v: 4308.
500 μF, 35 v: 4502 and 4503.
.0047 μF, 3000 v: 4812, 4813 and 4814.

Transistors:

2N222A: 2201, 2301 and 2401.
2N6044: 2202 and 2604.
IR 519: 2905.
MPQ2222: 2402, 2403, 2404, 2602, 2603, 2612, 2622, 2632, 2613, 2623 and 2633.
DTS 430: 2901, 2902, 2903 and 2904.

Resistors (all ¼ watt, 5% unless otherwise specified):

22K: 3201, 3302 and 3310.
10K: 3202, 3208, 3305, 3306, 3312, 3313, 3314, 3315, 3316, 3407, 3408, 3409, 3414, 3415, 3418, 3603, 3604, 3605, 3606, 3608, 3611, 3612, 3613, 3614, 3616, 3618, 3619, 3620, 3621, 3622 and 3704.
1K: 3203, 3206, 3404, 3410, 3411, 3412, 3413, 3416, 3417, 3420 and 3639.
47K: 3204 and 3905.
680: 3205 and 3406.
47: 3207.
10: 3209 and 3211 (10 watt).
27: 3212 and 3213.
301K: 3317.
15: 3405 (½ watt) and 3701.
2.7K: 3304.
330K: 3308.
220K: 3309, 3627, 3628, 3629, 3630, 3634 and 3709.
6.8K: 3402 and 3707.
27K: 3318, 3403 and 3419.
2.2K: 3501.
100K: 3631, 3632, 3633, 3706 and 3708.
33K: 3702.
8.2K: 3705.
11: 3710.
500: 3801 (10 watt), and 3811 (10 watt).
1 (25 watt): 3901, 3902, 3903 and 3904.

Diodes:

Zener 1N4744Z: 6201.
Zener 1N4751A: 6504.
1N4001: 6302, 6402, 6403, 6404, 6405, 6603, 6604, 6605 and 6606.

TABLE-continued

Zener 1N4735A: 6701.
Zener 1N4752A: 6601.
Full-wave bridge rectifier, 2 amp: 6501, 6502 and 6503.
Full-wave bridge rectifier, 12 amp: 6901.

Fuses:

1 amp: 8501 and 8502.
½ amp: 8503.
8 amp: 8801.
7.5 amp circuit breaker, dual pole: 8901.

In preparation for operation of the electrosurgical generator, a return electrode, preferably of relatively large area, should be applied to the patient and connected to the patient return terminal of the generator output. In addition, the electrode scalpel should be plugged into the monopolar output or the two bi-polar outputs as is appropriate for the particular electrode scalpel configuration.

Operation of the invention is begun by actuating circuit breaker 8901 to supply primary power to the power supply circuitry in FIG. 13. The mode switches 9901 and 9902 (FIGS. 1 and 3) are then adjusted to preset the mode to be activated during the course of surgery by selection of either the cut command or the coagulate command. Power levels to be applied during each operation mode are then set by adjusting potentiometers 3906 and 3907 (FIG. 3). These settings are visually indicated by the dual digital display systems (FIG. 6).

In order to initiate the surgical procedure, either of switches 510 or 512 may be closed to activate the cut command group; alternatively, either of switches 511 or 513 may be closed to activate the coagulate command group. The output signal from the electrode scalpel can be interrupted at any time, without adjusting the circuit breaker 8901, by opening the switch 510–513 which was closed to activate the operating command group or by closing another one of the switches to activate the opposite command group. In the latter case, or if the thermostat 9903 (FIG. 2) detects overheating of the output transistors, the command control automatically activates the appropriate lamp (7905, 7906, 7907, 7098, FIG. 3) and changes the output frequency of the tone generator (at operational amplifier 1497 and speaker 9906, FIG. 2) to indicate an automatic shut down of operation. If there is no automatic shut down, the command control activates the command line corresponding to the command switch which has been closed.

When either of command lines 201 or 202 is activated, the high frequency oscillator 115 and the timer 117 begin operation. In addition, if the pure cut command signal line 301 is activated, the one-shot multivibrator 1395 is triggered. As described above, the output pulse from the one-shot multivibrator 1395 prevents the low frequency signal generated at timer 117 from producing secondary modulation on the high frequency signal generated by oscillator 115. The pure cut mode is, therefore, characterized by an initial period wherein no secondary modulation appears on the high frequency signal. There is no primary modulation applied during the pure cut mode. If any of the other mode conditions are activated, the activated mode line 302–304 activates a particular division function at the variable frequency divider 119 to effect the necessary primary modulation of the high frequency signal. Whichever of mode lines 301–304 is activated, a corresponding output level amplifier 107, 109, 111 or 113, respectively, is also activated. The activated amplifier provides a signal corresponding to a previous adjustment at potentiometers 3906 and 3907 to effect control over the amplitude level at the main output amplifier 200. The voltage across the primary winding of output transformer 5801 is equal to the level of the d.c. voltage provided by voltage supply 123 minus the output signal level of amplifier 200. The current generated through the secondary winding of output transformer 5801 passes through a blocking capacitor to the electrode scalpel and is then returned through the patient return path or to the bipolar output terminal and the blocking capacitor coupled thereto. By providing the appropriate turns ratio for transformer 5801, the output impedance of the generator is matched to the relatively high impedance of a human joint which is subjected to the surgical procedure, thereby assuring efficient transfer of energy from the generator to the surgical site.

If the physician desires to switch between operation modes during a surgical procedure, the appropriate mode switch 9901 or 9902 can be manipulated. If one command group is de-activated and the other one initiated, the mode control automatically activates the appropriate mode line corresonding to the preset mode switch 9901 or 9902. Power levels of the output signal may also be continually adjusted by manipulating potentiometers 3906 or 3907.

It is to be understood that the 360 millisecond output pulse provided by one-shot multivibrator 1395 need not be 360 milliseconds. The important function provided by this pulse is to prevent secondary modulation from being applied to the high frequency cutting signal during the start up portion of the pure cut mode. Although a 360 millisecond interval has been found desirable for the start up feature, other start up time intervals are certainly considered as residing within the scope of the present invention. Generally, it is desirable that the start up time interval fall within a range of 100 to 500 milliseconds.

The 250 Hz frequency for the secondary modulation signal is also not to be considered as a limiting feature of the present invention. For example, the frequency of the secondary modulation signal can vary, as necessary, to achieve the desired on-off characteristics in the various operating modes. Likewise, the duty cycle of 60% described herein for the secondary modulation signal is not to be considered as a limiting feature of the present invention for the same reason.

The 475 KHz frequency utilized for the high frequency output signal from oscillator 115 is also to be considered as an example only and variation from that figure is to be included within the scope of the present invention.

While I have described and illustrated various specific embodiments of my invention, it will be clear that variations from the details of construction which are specifically illustrated and described may be resorted to without departing from the true spirit and scope of the invention as defined in the appended claims.

What I claim is:

1. An electrosurgical generator of the type in which a high frequency signal is generated to effect cutting, said generator comprising:
    means for generating said high frequency signal;
    terminal means for passing a cutting signal applied thereto to a patient;
    selectively actuable control means for permitting selective activation of a cut command signal;
    rapid start means responsive to activation of said cut command signal for applying said high frequency signal to said terminal means continuously for a predetermined time interval; and
    further means responsive to expiration of said predetermined time interval after activation of said cut command signal for cyclically and alternatively applying and inhibiting application of said high frequency signal to said terminal means such that each cycle of application and inhibition is very much shorter than said predetermined time interval.

2. The electrosurgical generator according to claim 1 wherein said predetermined time interval is in a range of 100 to 500 milliseconds, and wherein the time duration of each cycle of application and inhibition is in a range of 1 to 20 milliseconds.

3. The electrosurgical generator according to claim 2 wherein said predetermined time interval is approximately 360 milliseconds, and wherein said time duration of each cycle of application and inhibition is approximately 4 milliseconds.

4. The electrosurgical generator according to claim 3 wherein said time duration includes an approximately 2.5 millisecond portion during which said high frequency signal is applied to said terminal means and an approximately 1.5 millisecond portion during which application of said high frequency signal to said terminal means is inhibited.

5. The electrosurgical generator according to claim 2 wherein said time duration is subdivided into a first portion comprising approximately 60% of said time duration and during which said high frequency signal is applied to said terminal means, and a second portion comprising approximately 40% of said time duration during which application of said high frequency signal to said terminal means is inhibited.

6. The electrosurgical generator according to claim 1 further comprising:
    timer means for generating a repetitive gating signal which alternates cyclically between first and second amplitude levels;
    wherein said further means comprises gating means, connected to receive said repetitive gating signal and said high frequency signal, and responsive to activation of said cut command signal for passing said high frequency signal when said gating signal is at said first amplitude level and inhibiting passage of said high frequency signal when said gating signal is at second amplitude level; and
    wherein said rapid start means comprises first means responsive to activation of said cut command signal for generating an inhibit signal for said predetermined time interval, and second means responsive to said inhibit signal for inhibiting application of said gating signal to said gating means while instead applying a further signal at said second amplitude to said gating means.

7. The electrosurgical generator according to claim 6 wherein said gating signal has a duty cycle such that it is at said first amplitude for approximately 60% of the time and at said second amplitude for approximately 40% of the time.

8. The electrosurgical generator according to claim 7:
    wherein said control means further comprises means for selectively activating a second command signal alternatively to said cut command signal;
    said electrosurgical generator further comprising:

logic means responsive to activation of said second command signal for generating a first periodic modulation signal which alternates between two binary levels and which has a period which is greater than the period of said high frequency signal but which is considerably smaller than the period of said gating signal; and wherein said gating means is further responsive to said first periodic modulation signal for passing said high frequency signal when said first periodic modulation signal is at one binary level and for inhibiting passage of said high frequency signal when said first periodic modulation signal is at a second binary level.

9. The electrosurgical generator according to claim 8 wherein said control means further comprises:

means for selectively activating third and fourth command signals alternatively to one another and to said cut and second command signals;

wherein said logic means is responsive to activation of said third command signal for generating a second periodic modulation signal which alternates between two binary levels and which has a period which is greater than the period of said high frequency signal but considerably smaller than the period of said gating signal;

wherein said logic means is also responsive to activation of said fourth command signal for generating a third periodic modulation signal which alternates between two binary levels and which has a period greater than the period of said high frequency signal but considerably smaller than the period of said gating signal;

wherein said first, second and third periodic modulation signals have different duty cycles; and wherein said gating means is further responsive to said second and third periodic modulation signals for passing said high frequency signal when said second or third periodic modulation signal is at said one binary level and for inhibiting passage of said high frequency signal when said second or third periodic modulation signal is at said second binary level.

10. The electrosurgical generator according to claim 1 wherein said terminal means comprises an output transformer circuit having an output impedance which is greater than 1000 Ohms.

11. A method of electrosurgery comprising the steps of:

generating a high frequency signal of sufficiently high frequency to effect cutting of human tissue;

permitting selective activation of a cut command signal;

in response to activation of said cut command signal, applying said high frequency signal continuously for a predetermined time interval to terminal means for effecting cutting of human tissue; and in response to expiration of said predetermined time interval after activation of said cut command signal, cyclically and alternatively applying and inhibiting application of said high frequency signal to said terminal means such that each cycle of application and inhibition is very much shorter than said predetermined time interval.

12. The method according to claim 11 wherein said predetermined time interval is in a range of 100 to 500 milliseconds, and wherein the time duration of each cycle of application and inhibition is in a range of 1 to 20 milliseconds.

13. The method according to claim 12 wherein said predetermined time interval is approximately 360 milliseconds, and wherein said time duration of each cycle of application and inhibition is approximately 4 milliseconds.

14. The method according to claim 13 wherein said time duration includes an approximately 2.5 millisecond portion during which said high frequency signal is applied to said terminal means, and an approximately 1.5 millisecond portion during which application of said high frequency signal to said terminal means is inhibited.

15. The method according to claim 12 wherein said time duration is subdivided into a first portion comprising approximately 60% of said time duration during which said high frequency signal is applied to said terminal means, and a second portion comprising approximately 40% of said time duration during which application of said high frequency signal to said terminal means is inhibited.

16. The method according to claim 11 further comprising the steps of:

generating a repetitive gating signal which alternates cyclically between first and second binary amplitude levels;

in response to activation of said cut command signal, passing said high frequency signal when said gating signal is at said first amplitude level and inhibiting passage of said high frequency signal when said gating signal is at said amplitude level;

in response to activation of said cut command signal, generating and inhibit signal for said predetermined time interval; and in response to said inhibit signal, inhibiting said gating signal while permitting said high frequency signal to pass unmodulated.

17. The method according to claim 16 wherein said gating signal has a duty cycle such that it is at a first amplitude for approximatey 60% of the time and at a second amplitude for approximately 40% of the time.

18. The method according to claim 17 further comprising the steps of:

selectively activating a second command signal alternatively to said cut command signal;

in response to activation of said second command signal, generating a first periodic modulation signal which alternates between two binary levels and has a period which is greater than the period of said high frequency signal but considerably smaller than the period of said gating signal; and in response to said first periodic modulation signal, passing said high frequency signal when said first periodic modulation signal is at one binary level and inhibiting passage of said high frequency signal when said first periodic modulation signal is at said second binary level.

19. An electrosurgical generator comprising:

first and second command switches for selecting a command status of operation of said generator;

command control means coupled to said first and second command switches for preventing simultaneous activation of said first and second command switches;

a first mode switch for selecting a first mode of operation when the first command switch is activated;

a second mode switch for selecting a second mode of operation when the second command switch is activated;

mode control means coupled to said first and second mode switches for determining the mode of operation indicated by said first and second command switches and said first and second mode switches, said command control means being coupled to said mode control means by first and second command lines;

first, second, third and fourth voltage amplifiers, said amplifiers being coupled to said mode control means such that a respective amplifier, corresponding to the mode of operation indicated by said first and second mode switches and said first and second command switches, is activated by said mode control means;

a first NAND gate having input terminals coupled respectively to said first and second command lines;

high frequency oscillator means and low frequency oscillator means coupled to the output of said first NAND gate to activate said high and low frequency oscillator when either of said command lines is activated;

a three input NAND gate;

one-shot multivibrator means coupled to said mode control means to receive a triggering input at the onset of one particular mode of operation indicated by said first and second mode switches and said first and second command switches, said one-shot multivibrator means, once triggered, providing a timer pulse for a predetermined time interval;

OR gate means connected to receive the output of said low frequency oscillator means and said timer pulse, the output of said OR gate means being coupled to a first input of said three input NAND gate, wherein the output of said high frequency oscillator means is coupled to a second input of said three input NAND gate;

variable frequency divider means, the output of said high frequency oscillator means also being coupled to said variable frequency divider means, said variable frequency divider means also being coupled to said mode control means, the output of said variable frequency divider means being a first interrupt signal including a high voltage portion and a low voltage portion, the frequency of said first interrupt signal being an integral submultiple of the frequency of the output signal of said high frequency oscillator means, the ratio of the time duration of said high frequency voltage portion to the time duration of said low frequency voltage portion being altered by said variable frequency divider means to produce a surgical wave form corresponding to the mode of operation indicated by said first and second mode switches and said first and second command switches, the output of said variable frequency divider means being coupled to a third input of said three input NAND gate; and voltage controlled main amplifier, the output of said three input NAND gate being coupled to the input of said voltage controlled main amplifier, said voltage controlled main amplifier being coupled to said first, second, third and fourth amplifiers such that said amplifiers control the output level of said voltage controlled main amplifier.

20. The electrosurgical generator according to claim 19 further comprising isolation transformer means having a primary winding and at least one secondary winding, the output of said voltage controlled main amplifier being coupled through the primary winding of said isolation transformer means to a d.c. voltage supply, and wherein the output impedance presented across said secondary winding is at least 1,000 Ohms.

* * * * *